United States Patent
Becker

(10) Patent No.: US 9,662,451 B2
(45) Date of Patent: May 30, 2017

(54) RETROBULBAR SYRINGE AND METHODS OF USE

(76) Inventor: Bruce Becker, Encino, CA (US)

(*) Notice: Subject to any disclaimer, the term of this patent is extended or adjusted under 35 U.S.C. 154(b) by 1213 days.

(21) Appl. No.: 13/542,864

(22) Filed: Jul. 6, 2012

(65) Prior Publication Data

US 2013/0012919 A1 Jan. 10, 2013

Related U.S. Application Data

(60) Provisional application No. 61/504,858, filed on Jul. 6, 2011.

(51) Int. Cl.
*A61M 5/315* (2006.01)
*A61M 5/32* (2006.01)

(52) U.S. Cl.
CPC .......... *A61M 5/315* (2013.01); *A61M 5/3297* (2013.01); *A61M 5/326* (2013.01); *A61M 2005/3267* (2013.01)

(58) Field of Classification Search
CPC ........ A61M 5/315; A61M 2005/31598; A61M 5/31511; A61M 5/3243; A61M 5/3257
See application file for complete search history.

(56) References Cited

U.S. PATENT DOCUMENTS

| | | | |
|---|---|---|---|
| 2,869,543 A | 1/1959 | Ratcliff et al. | |
| 6,228,054 B1 | 5/2001 | Dysarz | |
| 6,584,910 B1 | 7/2003 | Plass | |
| 2004/0122359 A1* | 6/2004 | Wenz | A61M 5/31511 604/82 |
| 2010/0010468 A1* | 1/2010 | Becker | A61M 5/329 604/506 |

OTHER PUBLICATIONS

International Search Report and Written Opinion for PCT Patent App. No. PCT/US2012/045664 (Oct. 10, 2012).

* cited by examiner

*Primary Examiner* — Emily Schmidt
*Assistant Examiner* — Lauren M Peng
(74) *Attorney, Agent, or Firm* — Adam J. Cermak; Cermak Nakajima & McGowan LLP

(57) ABSTRACT

A device useful for making retrobulbar injections includes an inner syringe contained within an outer syringe. A spring retained within the outer syringe biases the inner syringe proximally, which a catch mechanism on the two syringes prevents the inner syringe from moving out of the outer syringe. A distal needle on the inner syringe is movable within a distal sheath of the outer syringe, and can be extended beyond the distal end of the sheath to permit the device to piece more resilient tissues, and can be withdrawn by action of the spring within the sheath to protect more delicate tissues from the needle.

10 Claims, 2 Drawing Sheets

RETROBULBAR SYRINGE AND METHODS OF USE

This application claims priority under 35 U.S.C. §119 to U.S. provisional application No. 61/504,858, filed 6 Jul. 2011, the entirety of which is incorporated by reference herein.

BACKGROUND

Field of Endeavor

The present invention relates to devices, systems, and processes useful as injection syringes, and more specifically to syringes useful for making retrobulbar injections.

Brief Description of the Related Art

Many ophthalmology procedures are performed with a local anesthetic and intravenous sedation. Retrobulbar or peribulbar (behind the eye or adjacent to the eye) injections of local anesthetic are often used for intraocular surgeries, such as cataract extraction, retinal, vitreous, corneal, and pterygium surgeries. Retrobulbar injections are typically performed by placing a 1½ or 1¼ inch needle through the lateral lower lid adjacent to the inferior orbital rim and pushing deep into the orbit. In some cases the needle may be directed superomedially when it is deep in the orbit. This movement is to permit better flow of local anesthetic into the orbital apex. The local anesthetic is injected after the needle is in place. The needle is then withdrawn. The purpose of the local anesthetic is to provide anesthesia and akinesia (prevent movements of the eye which is critical during delicate intraocular surgery).

Peribulbar injections of local anesthetic involve placing the needle through the lateral lower lid adjacent to inferior orbital rim. However, the needle is not pushed as deep into the orbit as with a retrobulbar injection.

During these procedures, the surgeon cannot visualize the needle or orbital structures with this technique; that is, the needle is placed blindly. Therefore, vital structures such as the optic nerve, blood vessels, and the eye cannot be avoided.

Many complications can occur during retrobulbar, and to a lesser extent peribulbar, injections of local anesthetic. A retrobulbar hemorrhage can occur if the needle encounters a blood vessel. A severe retrobulbar hemorrhage can place pressure on the optic nerve and cause blindness. The needle can also puncture the eye which may result in severe visual loss. The needle can also penetrate the optic nerve sheath. The injection of a commonly used anesthetic, bupivicaine, causes respiratory arrest in these cases.

An effort to avoid these complications has been the use of anesthetic eyedrops alone for cataract extractions. This technique is not possible in patients who are not cooperative and are too anxious. The use of anesthetic eyedrops alone is not possible for long surgeries such as retinal or vitreous surgeries. Retrobulbar anesthesia is still needed for patients who are anxious, unable to cooperate, or for retinal or vitreous surgeries, or corneal transplants.

An effort to reduce the complications of retrobulbar anesthetic injections is shown with the metal Atkinson retrobulbar needle. This needle is somewhat more rounded at the tip than typical needles used for local anesthetic injections. However, the needle is still sharp and metallic and can cause all of the complications listed above.

Another problem is that the injection is out the distal end of the needle only. The surgeon must angle the needle toward the optic nerve to make the anesthetic flow toward the orbital apex. This maneuver increases the rate of complications described above.

Needles are also used during other types of surgery for the injection of local anesthetic. In many procedures, the same syringe and needle are used repeatedly. That is because the local anesthetic effect may dissipate during the procedure, or the surgery may extend to more areas that were not anesthetized by the original injections. In other cases, areas of bleeding require additional injections to allow the epinephrine in the local anesthetic to constrict the blood vessels and stop the bleeding.

The same needle and syringe are used repeatedly because of the added time (and cost) to obtain a new needle for each of many injections. The cap must be placed on the needle between uses. The needle and syringe must be picked up, placed on a tray, handed from the surgical technician to the surgeon and vice versa, and otherwise handled. All of these maneuvers place the operating personnel at a risk for an accidental needle stick and the transmission of disease such as HIV and hepatitis C.

There are various safety needles for injections and the placement of intravenous lines available. However, all of these needles and intravenous needles/lines are for a single use only.

U.S. patent application Ser. No. 12/496,431, filed 1 Jul. 2009, and published as U.S. Patent Application No. 2010/0010468 A1, by Bruce Becker ("'431 application"), the inventor herein, describes several useful and innovative needles and syringes, which is incorporated by reference herein.

SUMMARY

According to a first aspect of the invention, a retrobulbar syringe comprises an inner syringe having a hollow barrel with a proximal end, a distal end, an outer barrel surface, a plunger in the barrel, and a needle attached to the barrel distal end, an outer syringe having a hollow barrel with a proximal end, a distal end, an barrel inner surface, and a sheath attached to the outer syringe barrel distal end, wherein the inner syringe is at least partially contained in the outer syringe barrel, and wherein the needle is at least partially contained and movable in the sheath, a spring inside the outer syringe barrel bearing against the inner syringe and biasing the inner syringe toward the outer syringe proximal end; and a first locking member on the inner syringe barrel outer surface, and a second locking member on the outer syringe barrel inner surface, the first and second locking members being configured and arranged to inhibit the inner syringe from being moved proximally out of the outer syringe barrel.

According to another aspect of the present invention, a method for inserting a needle into a patient's orbit, wherein said needle is contained in a sheath and is moveable in and out of said sheath, comprises squeezing two syringes together, including causing a distal tip of the needle to extend out of a distal end of the sheath, pushing said syringes, the needle, and the sheath through the patient's skin with at least the distal tip of the needle extending out of the distal end of the sheath, stopping said squeezing and allowing the needle tip to retract inside the sheath, pushing said syringes with the needle further into the orbit with the needle retracted inside the sheath, contacting delicate structures of the orbit with a softer distal end of the sheath, and pushing a plunger on an inner syringe of the two syringes and injecting an anesthetic into the orbit.

According to yet another aspect of the present invention, a method of retracting a needle into a sheath, wherein the needle tip is contained in a proximal higher durometer segment of the sheath, comprises protecting delicate orbital structures from damage by the needle with the proximal portions of the sheath after inserting the needle into a patient's orbit.

According to another aspect of the present invention, a method of preventing an inner syringe from detaching from an outer syringe, comprises providing the syringes with rings on the outer surface of the inner syringe on the inner surface of the outer syringe.

According to another aspect of the present invention, a method of placing an inner syringe into an outer syringe, comprises providing the syringes with rings on the outer surface of the inner syringe and on the inner surface of the outer syringe, the rings each having a triangular cross-section, and placing the inner syringe inside the outer syringe, including pushing oppositely oriented faces of the rings of the inner and outer syringes against each other.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which.

DETAILED DESCRIPTION OF EXEMPLARY EMBODIMENTS

Figure 1:
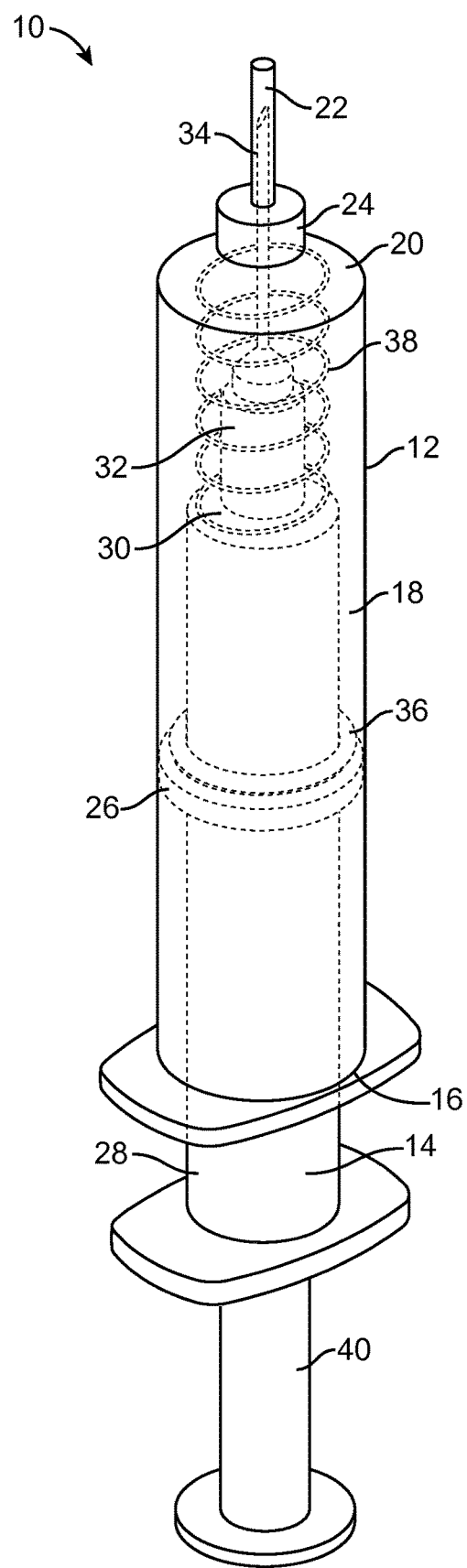
FIG. 1 illustrates a perspective view of an exemplary device with a needle thereof withdrawn proximally of the distal tip of a sheath thereof.

Referring to the drawing figures, like reference numerals designate identical or corresponding elements throughout the several figures.

The '431 application described a retrobulbar needle that protects the delicate structures of the orbit and eye from injury and reduces complications during retrobulbar or peribulbar anesthetic injections. Retrobulbar needles and syringes as described herein accomplish this with a design that is less costly to manufacture.

Figure 2:
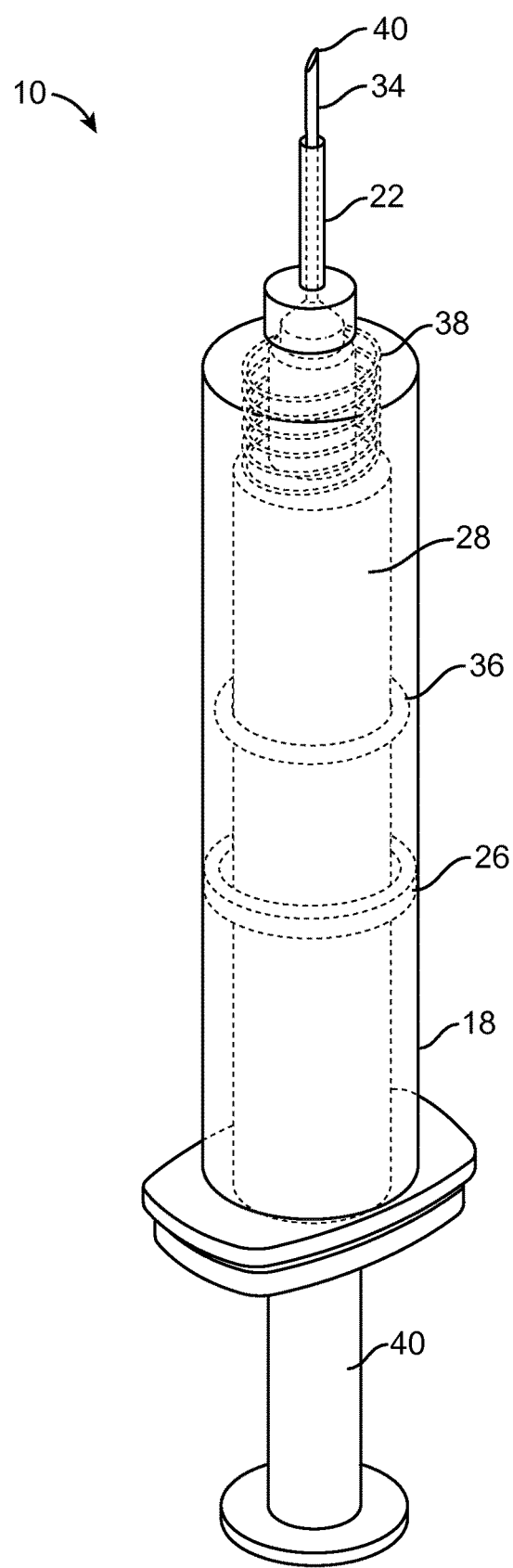
FIG. 2 illustrates a perspective view of an exemplary device with a needle thereof extended distally of the distal tip of the sheath thereof.

As illustrated generally in the FIGS. 1 and 2, a first exemplary embodiment of a syringe 10 adhering to principles of the present invention is illustrated. The syringe 10 includes an outer syringe 12 and an inner syringe 14. The outer syringe 12 is usually a 12 or 10 cc syringe, and the inner syringe 14 is usually a 5 or 6 cc syringe; however, other sizes may be used. A key characteristic is that the inner syringe 14 fits inside the outer syringe 12.

The outer syringe 12 has a hollow barrel 18, typical of syringes, with an open proximal end 16 and a closed distal end 20. A cannula 22, having a lumen therein, is attached to the end 20 via a hollow hub 24 in a known manner, and fluidly communicates the interior of the barrel with the exterior of the syringe 10. The outer syringe 12 also includes a holder or stop 26 formed on the inner surface of the barrel 18, and extends radially inwards from the barrel. The stop 26 is, in the embodiment of FIGS. 1 and 2, formed as a continuous ring; however, in other embodiments, the stop can be a series of one or more discontinuous projections from the inner surface of the barrel.

The inner syringe 14 is constructed in the manner of a typical, commercially available syringe, except as noted herein, and includes a hollow barrel 28, a plunger 40 movable in the barrel 28, a closed distal end 30, a needle hub 32, and a hollow, sharpened needle 34 extending distally from the hub and fluidly communicating the interior of the barrel 28 with the exterior of the syringe. The inner syringe includes a catch or stop 36 on the exterior of the barrel 28, which cooperates with the stop 26 to prevent the inner syringe 14 from moving too far proximally relative to the outer syringe 12, for the reasons discussed below. As with the stop 26, the stop 36 is, in the embodiment of FIGS. 1 and 2, formed as a continuous ring; however, in other embodiments, the stop 36 can be a series of one or more discontinuous projections from the outer surface of the barrel. A resilient member 38, in the illustrations embodied as a coil spring, is positioned on the outer surface of the distal end 30 of the inner syringe, and also is positioned against the inner surface of the distal end 20 of the outer syringe 12. The resilient member 38 is sized and configured so that the inner syringe 14 cannot slide past the member 38; when the member 38 is a coil spring, for example, the spring is sized to fit around the hub 32, but radially smaller than the barrel 28.

As described above, the outer syringe 12 has a holder or stop attached to the inside of the barrel. The holder is positioned between the distal and proximal ends of the syringe barrel. In other embodiments, however, it could be positioned at the proximal end of the barrel. The ring usually extends 360 degrees around the inside of the barrel, as is illustrated, but may be less than 360 degrees or have multiple segments. The inner syringe 14 has a catch that is formed on the outside of the barrel. The catch may extend 360 degrees around the barrel or less than 360 degrees, and the catch may have one or more than one segments. According to one exemplary embodiment, the catch is triangular shape when viewed in cross section. The side of the triangle facing the proximal end of the syringe is perpendicular to the syringe barrel. The second side of the triangle is the syringe barrel. The third side of the triangle faces the distal end of the syringe and forms an acute angle with the syringe barrel. The outer diameter of the catch 36 on the inner syringe 14 is slightly greater than the inner diameter of the holder 26 on the outer syringe 12. During the manufacturing process (after the placement of the spring 38 and needle 34), the inner syringe 14 is pushed inside the outer syringe 12 until the inner syringe catch is pushed distal to the outer ring holder. This is possible because the syringes 12, 14 are made of material that is slightly flexible. The inner syringe catch is thus permanently kept inside the outer syringe holder because of the shape of the two stops, which keeps the inner syringe from falling out of the outer syringe during usage.

Prior to placement of the inner syringe 14, the needle 34 with hub 32 is mounted, e.g., screwed, into the distal end of the inner syringe. The needle 34 usually has a 22 degree beveled end 40 that is less traumatic to tissues than typical needles; however, the needle end may be of any shape.

Prior to placement of the inner syringe 14 inside the outer syringe 12, the resilient member 38, e.g., spring, is placed. The spring has a diameter smaller than the inside diameter of the outer syringe. The spring has a diameter that is large enough to fit over the threaded segment on the distal end of the inner syringe. The inner diameter of the spring is smaller than the outside diameter of the inner syringe barrel.

The cannula or sheath 22, with the hub 24 on its proximal end, is mounted, e.g., screwed, into the distal end of the outer syringe 12. The sheath has a higher Durometer (hardness) proximal end and a lower Durometer distal end. The usual length of the sheath is 1¼ inch but may be shorter or longer. The distal ¼ inch of the sheath is softer that the proximal portions of the sheath, but the length of the distal softer end may be shorter or longer.

The manufacturing process involves the placement of the needle 34 on the distal end of the inner syringe 14. The sheath 22 is placed on the distal end of the outer syringe 12 (alternatively, the sheath may be placed on the distal end of the outer syringe as the last step in the manufacturing process). The spring 38 is then placed inside the outer syringe 12. The inner syringe 14 with the plunger 40 and needle 34 is placed inside the outer syringe 12 and pushed in until the catch 36 on the inner syringe is distal to the holder 26 on the outer syringe. The needle 34 is slid inside the sheath during the placement of the inner syringe into the outer syringe.

Example of use of the retrobulbar needle and syringe

With continued reference to FIGS. 1 and 2 together, the health care professional removes the plunger from the inner syringe. Local anesthetic is squirted or otherwise placed inside the inner syringe. The plunger is placed back into the inner syringe. The syringe is turned with the needle facing up and any air is pushed out the needle by pushing on the plunger.

The physician grasps the retrobulbar syringe. He pushes on the handle of the inner syringe while placing counter traction on the handle of the outer syringe. This pushes the inner syringe toward the distal end of the outer syringe while compressing the spring. This simultaneously pushes the needle 34 out of the sheath 22, and more specifically pushes the sharpened distal end of the needle distal of the distal end of the sheath 22, exposing the distal end of the needle.

The physician then pushes the syringe and exposed distal end of the needle through the patient's lower lid, usually temporally adjacent the inferior orbital rim through the lid skin and orbital septum. Alternatively, the needle can be pushed through any part of any lid into the orbit. The sheath around the needle also goes through the lid skin and orbital septum into the orbital fat. The needle is required to penetrate the more resistant skin and orbital septum. The sheath is now in the soft orbital fat. The physician releases the pressure with his fingers on the handles of the syringes. This allows the spring to push the inner syringe proximally relative to the outer syringe. This movement causes the needle to retract into the higher Durometer segment of the sheath. The needle thus cannot harm any orbital or ocular structures when it is completely inside the sheath.

The syringe and sheath are now pushed deeper into the orbit. Only the soft distal end of the sheath contacts structures inside the orbit (e.g., nerves, blood vessels, muscles) or eye. This prevents harm to these delicate structures. The physician now pushes on the plunger, thus causing the contents of the inner syringe barrel (e.g., local anesthetic) to be injected into the orbit. The syringe and sheath are now removed.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

I claim:

1. A retrobulbar syringe comprising:
    an inner syringe having a hollow barrel with a proximal end, a distal end, an outer barrel surface, a plunger in the barrel, and a needle attached to the barrel distal end;
    an outer syringe having a hollow barrel with a proximal end, a distal end, an barrel inner surface, and a sheath attached to the outer syringe barrel distal end, wherein the inner syringe is at least partially contained in the outer syringe barrel, and wherein the needle is at least partially contained and movable in the sheath;
    a spring inside the outer syringe barrel bearing against the inner syringe and biasing the inner syringe toward the outer syringe proximal end;
    a first locking member on the inner syringe barrel outer surface, and a second locking member on the outer syringe barrel inner surface, the first and second locking members being configured and arranged to inhibit the inner syringe from being moved proximally out of the outer syringe barrel;
    wherein at least one of the first and second locking members comprises a ring extending entirely around the inner syringe barrel or the outer syringe barrel, respectively.

2. A retrobulbar syringe according to claim 1, wherein the first and second locking members are configured and arranged to prevent the inner syringe from being moved proximally out of the outer syringe barrel.

3. A retrobulbar syringe according to claim 1, wherein the first and second locking members are configured and arranged to permit the inner syringe to be pushed distally into the outer syringe barrel with at least a portion of the needle extended distally from the sheath.

4. A retrobulbar syringe according to claim 1, wherein the first and second locking members both comprise triangularly shaped, oppositely oriented elements.

5. A retrobulbar syringe according to claim 1, wherein both of the first and second locking members comprises a ring extending entirely around the inner syringe barrel or the outer syringe barrel, respectively.

6. A retrobulbar syringe according to claim 1, wherein the sheath comprises a proximal portion and a distalmost portion, the hardness of the distalmost portion being less than the hardness of the proximal portion.

7. A method for inserting a needle into a patient's orbit, wherein said needle is contained in a sheath and is moveable in and out of said sheath, the method comprising:
    squeezing two syringes together, the syringes including rings on an outer surface of an inner syringe and on an inner surface of an outer syringe, including causing a distal tip of the needle to extend out of a distal end of the sheath;

pushing said syringes, the needle, and the sheath through the patient's skin with at least the distal tip of the needle extending out of the distal end of the sheath;

stopping said squeezing and allowing the needle tip to retract inside the sheath;

pushing said syringes with the needle further into the orbit with the needle retracted inside the sheath;

contacting delicate structures of the orbit with a softer distal end of the sheath;

pushing a plunger on an inner syringe of the two syringes and injecting an anesthetic into the orbit; and moving the inner syringe distally away from the sheath a distance sufficient so that the ring on the outer surface of the inner syringe is distal of and trapped distally behind the ring on the inner surface of the outer syringe.

8. The method of claim 7, wherein said squeezing comprises compressing a spring and causing the inner syringe to move distally and the needle tip to extend out the distal end of the sheath.

9. The method of claim 7, wherein said stopping the squeezing comprises expanding the spring and retracting the needle into the sheath.

10. The method of claim 7, wherein the rings are triangular in shape and opposite in orientation.

* * * * *